US00PP24419P3

(12) United States Plant Patent
Nystrom

(10) Patent No.: US PP24,419 P3
(45) Date of Patent: May 6, 2014

(54) APPLE TREE, 'CN B110'

(50) Latin Name: *Malus domestica*
Varietal Denomination: CN B110

(76) Inventor: Charles Nystrom, Worthington, MN (US)

( * ) Notice: Subject to any disclaimer, the term of this patent is extended or adjusted under 35 U.S.C. 154(b) by 128 days.

(21) Appl. No.: 13/506,992

(22) Filed: May 30, 2012

(65) Prior Publication Data

US 2013/0326770 P1 Dec. 5, 2013

(51) Int. Cl.
*A01H 5/00* (2006.01)

(52) U.S. Cl.
USPC ..... Plt./161

(58) Field of Classification Search
USPC ..... Plt./161
See application file for complete search history.

(56) References Cited

U.S. PATENT DOCUMENTS

PP7,197 P * 3/1990 Luby et al. ..... Plt./161

* cited by examiner

*Primary Examiner* — Wendy C Haas
(74) *Attorney, Agent, or Firm* — Paine Hamblen, LLP

(57) ABSTRACT

A new and distinct variety of apple tree is described and which is characterized as to novelty by producing an attractively colored apple which is mature for harvesting and shipment approximately October 12 under the ecological conditions prevailing in central, Washington state.

5 Drawing Sheets

Latin name: *Malus domestica.*
Varietal denomination: 'CN B110'.

BACKGROUND OF THE NEW VARIETY

The present invention relates to a new and distinct variety of apple tree, hereinafter designated as 'CN B110', and more specifically, to a new apple tree which produces fruit which are mature for harvesting and shipment under the ecological conditions prevailing in Grant County, Wash. at or about October 12$^{th}$.

ORIGIN AND ASEXUAL REPRODUCTION

The inventor removed seeds from open pollinated "Honeycrisp' apple trees (U.S. Plant Pat. No. 7,197) which were then growing in his commercial orchard which is located near 29716 Read Ave., Worthington, Minn. during the 1993 growing season. The aforementioned orchard is located in USDA Hardiness Zone 4b. The collected seeds were then planted in 1994 and successful seedlings were grown and then maintained on their own roots until the 2004 harvesting season. At that time, the promising new variety 'CN B110' was identified and named. After identification of the promising seedling, second generation trees were made by removing budwood and budding the new variety onto EMLA 9 rootstock (unpatented) and then planting the newly produced trees in a commercial nursery which is located in Ephrata, Grant County, Wash. in 2005. The new, second generation trees have been continually observed, and in 2011 produced fruit which could be observed. At this time, it was found that the new, second generation trees appeared to produce fruit which were substantially identical to that observed and produced by the original chance seedlings which were previously grown in Minnesota.

SUMMARY OF THE NEW VARIETY

The new variety 'CN B110' is a late-mid season ripening apple tree which is mature for harvesting and shipment some 11 days after the date of harvesting of the fruit produced by the 'Honeycrisp' apple tree (U.S. Plant Pat. No. 7,197) when it is grown under the same ecological conditions. In particular, the new variety of apple tree produces fruit having a shape which is much flatter than it is round. Still further, the fruit of the new variety has an excellent taste with the fruit having a very firm crisp texture, and exceptionally juicy characteristics. Still further, the fruit has a mildly subacid-like taste and is considered much better in relative comparison to the fruit produced by the 'Honeycrisp' apple tree (U.S. Plant Pat. No. 7,197) when grown under similar ecological conditions. Still further, the present variety of apple tree has demonstrated that it has a greater storage life than the fruit produced by the 'Honeycrisp' apple tree (U.S. Plant Pat. No. 7,197) and further retains its crispness following prolonged storage.

Figure 1:
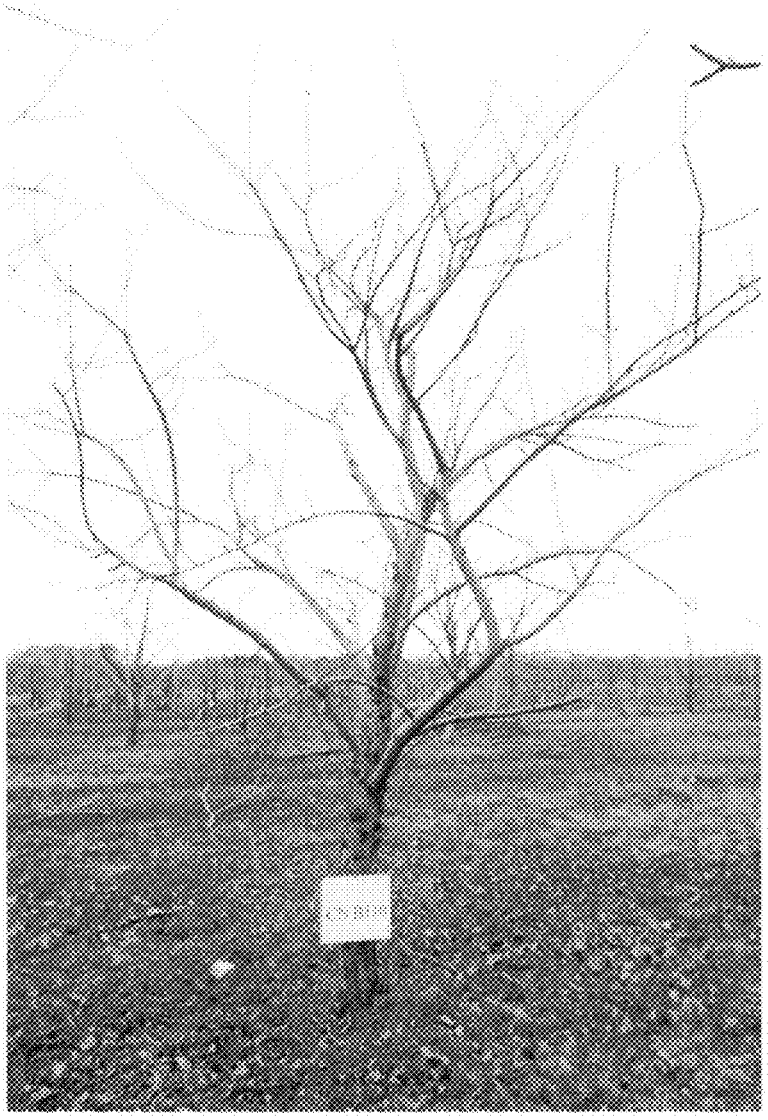
FIG. 1 is a view of the original dormant mother tree of the variety 'CN B110' growing in the orchard of origin.
Figure 2:
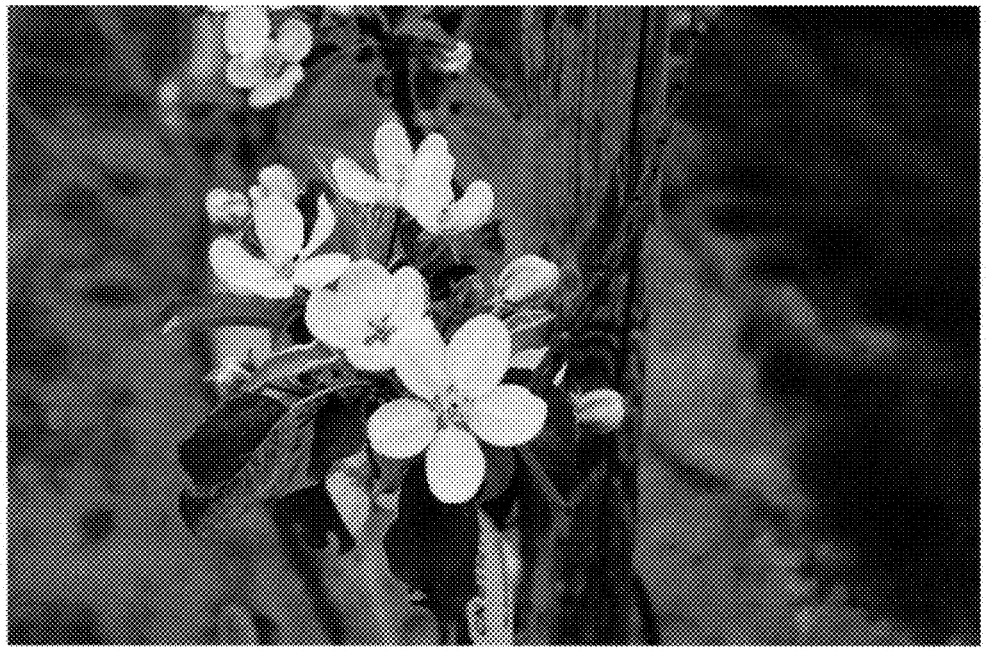
FIG. 2 illustrates the typical bloom as seen on second generation trees currently growing in Grant County, Wash.
Figure 3:
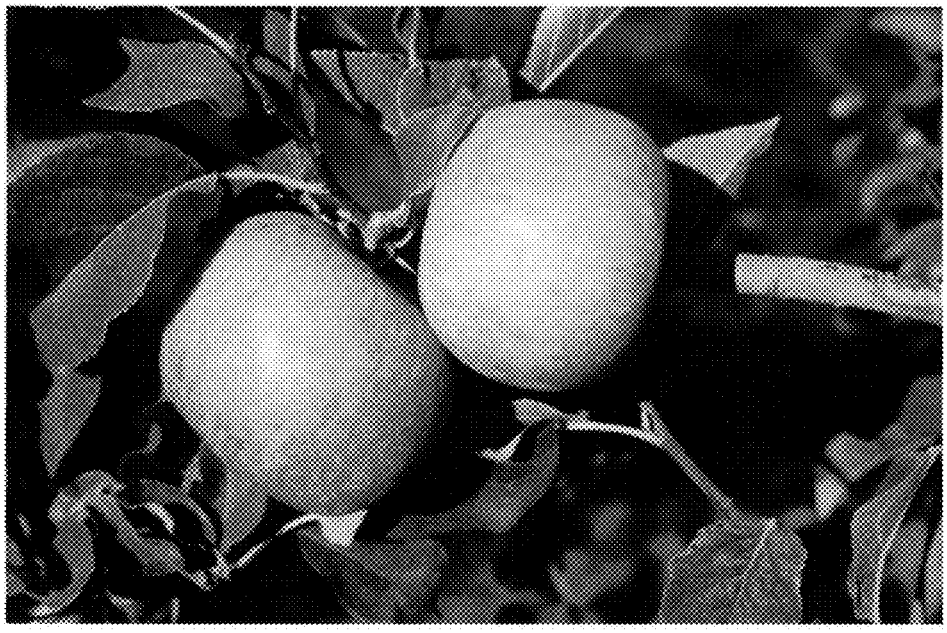
FIG. 3 illustrates a typical fruiting spur produced by a second generation tree growing in Grant County, Wash.
Figure 4:
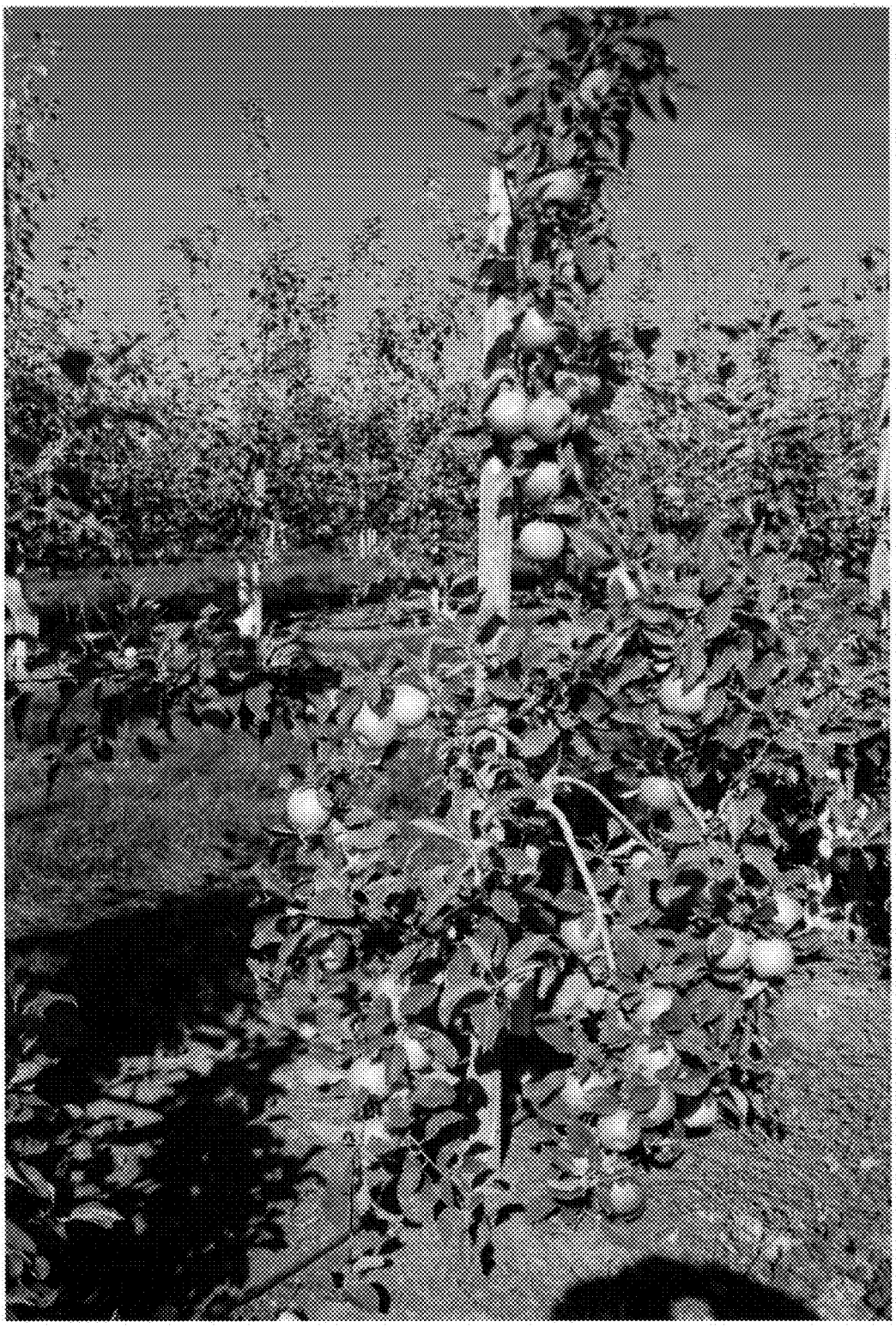
FIG. 4 shows the fruiting characteristics of a second generation 'CN B110' apple tree growing in Grant County, Wash.
Figure 5:
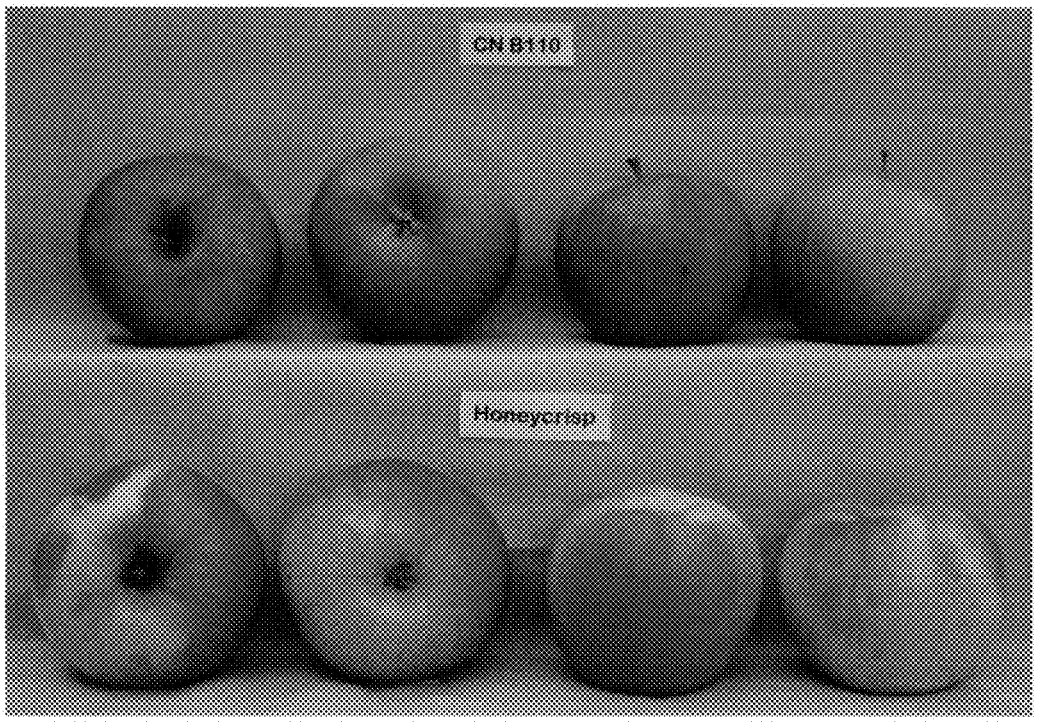
FIG. 5 shows a picture which compares the fruit produced by the new variety 'CN B110' relative to that produced by the 'Honeycrisp' apple tree when grown under similar ecological conditions.

The colors in the enclosed photographs are as nearly true as is reasonably possible in color photographs of this type. However, due to chemical development, processing and printing, the leaves and fruit depicted in these photographs may or may not be accurate when compared to the actual botanical specimens. For this reason, future color references should be made to the color plates (Royal Horticultural Society of Great Britain) and other common color descriptions as provided hereinafter.

NOT A COMMERCIAL WARRANTY

The following detailed description has been prepared to solely comply with the provisions of 35 U.S.C. §112, and does not constitute a commercial warranty, (either expressed or implied), that the present variety will in the future display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

TREE

*Size.*—Generally — The tree as described hereinafter is a three year old, second generation tree which is currently growing in Grant County, Wash. All major color code references are from The R.H.S. Colour Chart ($4^{th}$ Edition) and which is provided by The Royal Horticulture Society of Great Britain.
*Type.*—The present variety is trained, and grows on a central leader type system. Generally speaking, the present variety displays heavy spur development, and is considered precocious.
*Vigor.*—Considered moderate relative to other species.
*Overall shape.*—Considered upright, and spreading.
*Tree height.*—About 8 feet.
*Crown diameter.*—About 6.5 feet.
*Hardiness.*—Considered hardy for the current region it is being grown in, that being (USDA zone 6a).
*Fruit productivity.*—Considered highly productive.

TRUNK

*Size.*—About 2.5 cm. in diameter when measured at a height of about 20 cm. above the graft union.
*Bark texture.*—Considered rough, and sand-paper like.
*Bark color.*—Grey-orange (RHS Group 166A).
*Lenticels.*—Numbers — Present and numerous in number. The lenticels average about 14 per 4 sq. cm. area. The lenticel shape is elongated, and oriented substantially horizontally.
*Lenticel.*—Width — About 1 mm.
*Lenticel.*—Length — About 2.7 mm.
*Lenticel color.*—White (RHS N155D).

BRANCHES

First year branches:
*Diameter.*—About 4.6 to 5.2 mm. in diameter.
*Length.*—Current season growth is from about 5.5 cm. to about 43.2 cm.
*Bark color.*—Grey-orange (RHS 177A).
*Lenticels.*—Generally speaking they are numerous and average about 15 per running cm. of length. The lenticels are elongated in shape, although occasionally a few round ones may be found. The lenticels are oriented vertically. The lenticel length ranges from about 0.7 to 1.1 mm. Still further, the lenticel diameter ranges from about 0.3 to about 0.5 mm.
*Lenticel color.*—White (RHS N155D).
*Internode length.*—The distance between nodes ranges from about 2.8 to 3.6 cm.
*Branch pubescence.*—Present but considered light to moderate, and white in color. This color is not distinctive of the present variety.

Two year old fruiting branches:
*Diameter.*—About 8.2 mm. to about 15.3 mm.
*Spur development.*—Considered moderate.
*Bud length.*—About 9 mm. to about 11.5 mm.
*Bud diameter.*—About 4.1 mm. to about 5.1 mm.
*Bud color.*—Grey-purple (RHS 187A).
*Lenticels.*—Generally speaking lenticels are present, and average about 3 per sq. cm. The lenticels are oval in shape and have an average size of about 1.1 mm. by about 1.5 mm. The lenticel color is white (RHS 155C).
*Bark color.*—Grey-brown (RHS 199A).

Scaffold branches:
*Size.*—About 10.4 mm. to about 13.3 mm. in diameter.
*Crotch angle.*—As presently trained on a central leader system, the crotch angles range from 60 to about 70 degrees when measured from a vertical plane.
*Color.*—Grey-brown (RHS 199A).
*Lenticels.*—Generally speaking, the lenticels are moderate in number and average about 8 per sq. cm.
*Lenticels.*—Shape — Variable and being generally characterized as elongated and thin. The lenticels range in length from about 1 mm. to about 1.7 mm., and have a width of about 0.1 to about 0.3 mm.
*Lenticels.*—Orientation — Considered horizontal.

LEAVES

*Shape.*—Generally — Considered broadly acute and having some upward lifting of the leaf surface.
*Texture.*—Upper surface — Considered leathery and undulating.
*Texture.*—Lower surface — Considered glabrous.
*Sheen.*—The upper or dorsal surface has a high sheen.
*Pubescence.*—The leaves of the present variety display some light pubescence on the upper and lower surfaces. The lower surface is nearly completely covered and is moderate in density.
*Leaf pubescence.*—Color — Grey-yellow (RHS 160A).
*Leaf length.*—About 81.1 mm. to about 106.9 mm.
*Leaf width.*—About 43.2 mm. to about 69 mm.
*Leaf marginal edge.*—Considered mostly serrate and occasionally bi-serrate regions are found.
*Leaf tip.*—Shape — Acuminate.
*Leaf base.*—Shape — Rounded.
*Stipules.*—Generally — Present and normally two stipules are found per leaf.
*Stipule.*—Length — About 7.7 mm to about 14.4 mm.
*Stipule.*—Width — About 2 mm to about 3.2 mm.
*Stipule.*—Color — The dorsal surface has a yellow-green color (RHS 144B). The ventral surface is yellow-green (RHS 147B).
*Stipule.*—Pubescence — This is present on the ventral surface, and is considered fine, and covers nearly the entire surface. The color of this pubescence is grey-yellow (RHS 160A).

*Leaf blade color.*—Dorsal surface — Yellow-green (RHS 147A); Ventral surface — Yellow-green (RHS 147B).

*Leaf mid-vein.*—Shape — Considered prominent, and having a fine pubescence which is located under the vein.

*Mid-Vein.*—Diameter — At mid-blade it is about 1.1 to about 1.6 mm.

*Mid-Vein.*—Upper surface color — Yellow-green (RHS 145D).

*Mid-vein pubescence.*—The pubescence covers nearly 100 percent of the lower surface and has a color of grey-yellow (RHS 160A).

*Petiole.*—Length — About 25.4 mm. to about 32.5 mm. per inch.

*Petiole.*—Shape — A shallow groove extends the entire length of the upper surface of the petiole.

*Petiole.*—Diameter — At the mid point of the petiole, this is about 1.5 mm. to about 2.3 mm.

*Petiole color.*—Upper surface — Yellow-green (RHS 144B).

*Petiole color.*—Lower surface — Yellow-green (RHS 145C). Occasionally, a light highlight is found at the basal end of the petiole, and has a color of grey-red (RHS 180A).

*Petiole pubescence.*—Considered moderate in density over the entire length and circumference of the petiole.

*Petiole pubescence color.*—Grey-yellow (RHS 160A).

FLOWER

*Full bloom.*—Full bloom was achieved on May 9, 2011.

*Number of blossoms per bud.*—This ranges from 3 to 5, mostly 4.

*Flower size.*—Considered average for the species. When fully expanded the diameter of the flowers ranged from 41 to 48 mm.

*Petal width.*—About 13 to 18 mm. Petal Length. — About 17 to 23 mm.

*Petal color.*—White (RHS N155B). The dorsal surface has color highlights from the Grey-Purple group (RHS 186D), and the basal vein color is Grey-Purple (RHS 186C).

*Stamens.*—Number — From 19 to 21.

*Filament length.*—About 4.1 to about 11.4 mm. Filament color is Yellow (RHS 4C).

*Anthers.*—Shape — Kidney like, and having a width of about 2.1 mm., and a length of about 2.6 mm.

*Anthers.*—Color — At full maturity it is Yellow (RHS 5D).

*Pistil.*—Length — about 14 to 14.9 mm.

*Styles.*—Numbers — 5. Generally speaking, the styles are fused at about half the distance from base, and are white, pubescent at the union at the base.

*Style color.*—Yellow-Green (RHS 145B).

*Stigma.*—Round and club shaped. Stigma diameter is about 0.8 to 0.9 mm. The stigma color is Yellow-Green (RHS N144B).

*Sepals.*—Numbers — 5 per blossom are typically found.

*Sepals.*—Shape — considered deltoid, and the tip shape is acuminate and the base is truncate in form.

*Sepals.*—Length — About 8.1 mm. Sepals Width — about 3.9 mm.

*Sepals pubescence.*—Abundant White pubescence is found on both the upper and the lower surfaces. The sepal color is Yellow-Green (RHS 144A). Sepal tips are highlighted with a Grey-Orange color (RHS 166A).

*Peduncle.*—Length — about 27 to 35 mm.

*Peduncle.*—Color — Yellow-Green (RHS 144A).

FRUIT

Generally speaking, the foregoing observations of the fruit were taken from second generation trees (3 year old) growing under the ecological conditions prevailing in Ephrata, Grant County, Wash. in 2011.

*Fruit form.*—Considered flat and round, and occasionally lopsided, and somewhat irregular.

*Size.*—Considered average for the species with normal crop loading.

*Average equatorial diameter.*—About 77.3 to 83.9 mm.

*Average axial diameter.*—About 62.8 to 71.5 mm.

*Stem.*—Length — Considered long, and medium slender for the variety. Typically a small fleshy growth appears about 20-50% of the distance from the stem bowl base. Stem length is about 20.9 to 32.5 mm. Stem Diameter is about 1.9 to 2.5 mm.

*Stem cavity.*—Shape — The stem cavity does not appear lipped and is fully russeted. The russeting spills onto the shoulders of the fruit.

*Stem cavity.*—Width — About 31.5 to 34.7 mm.

*Stem cavity.*—Depth — About 15.7 to 19.3.

*Cavity shape.*—Acuminate.

*Basin cavity.*—Shape — Considered wide and having indistinct to light crowning and ribbing.

*Basin cavity.*—Width — About 27.3 to 35.3 mm.

*Basin cavity.*—Depth — Ranges from 7.2 to 16.3 mm.

*Eye.*—Erect and having nearly convergent tips.

*Sepal color.*—Green (RHS 138B).

*Sepal texture.*—Considered downy, and having a White color (RHS 155C).

*Skin.*—Surface Texture — Smooth, and occasionally having a small amount of light russeting which develops around the existing lenticels.

*Bloom.*—Amount — Considered moderate for the species.

*Skin texture.*—Considered tender.

*Skin thickness.*—Considered thin for the species.

*Skin appearance.*—Appearing blotched and marbled.

*Skin color.*—Generally — A red over stripe color is present, and is characterized as (RHS 46B); a red over color is also present (RHS 47A); a yellow-green under color is also evident (RHS 154D).

*Lenticels.*—Present, but they are considered rather inconspicuous. The lenticels are round, and smooth and generally regularly distributed.

*Lenticels.*—Numbers — About 10 per square cm.

*Lenticel color.*—Orange-White (RHS 159D).

*Lenticel size.*—About 0.3 to 0.6 mm. in diameter.

*Fruit core.*—Position — Considered distant.

*Fruit core line position.*—Basal clasping.

*Core diameter.*—About 37.0 mm.

*Core length.*—About 25 mm.

*Core shape.*—Considered flat and conical.

*Fruit cell.*—Numbers — 5.

*Fruit cell shape.*—Obovate.

*Fruit cell length.*—About 13.8 mm.

*Fruit cell width.*—About 9.2 mm.

*Fruit cell.*—Depth — About 4.4 mm.

*Tube.*—Shape — Cone shaped.

*Stamen position.*—Generally — Considered basal.

*Fruit axis.*—Form — Axile and open.

*Fruit seeds.*—Number — Typically 2.

*Seed shape.*—Acute. Seed Length — about 8.3 to 9.3 mm, Seed Width about 4.8 to 5.7 mm.

*Seed color.*—Brown (RHS 200B).

*Flesh.*—Firmness and Flavor — The variety Is considered to produce fruit flesh which is firm, crisp, and melting, and mildly sub-acidic, and further having a very juicy and mild apple flavor.

*Flesh color.*—Yellow (RHS 2D).

*Aroma.*—Having a very mild apple aroma.

*Date of harvesting.*—About October 12, in 2011 under the ecological conditions then prevailing in Grant County, Wash. state.

*Fruit pressure.*—Generally — The present variety, upon harvesting, had a fruit pressure of about 19 pounds as compared to the fruit produced by the 'Honeycrisp' apple trees (U.S. Plant Pat. No. 7,197), and which were grown under similar ecological conditions, and which had a fruit pressure of about 14.5 pounds. When measured on Jan. 23, 2012 the fruit pressure of the new variety measured 18 pounds, while the fruit of the 'Honeycrisp' apple tree had a fruit pressure of 13.5 pounds.

*Brix.*—Upon harvesting the fruit of the present variety had a brix of about 13.9 as compared to the fruit of the closest known variety 'Honeycrisp', and which had a brix of 11.1 When measured on Jan. 23, 2012 the fruit of the new variety had a brix of 14.2 as compared to the brix of the fruit of the 'Honeycrisp' apple tree which was measured as 12.2.

*pH.*—Upon harvest the fruit of the new variety had a pH of about 3.49, as compared to the pH of the fruit produced by the 'Honeycrisp' apple tree, and which was measured as 3.3. When the pH was again measured on Jan. 23, 2012 the pH of the new variety was measured as 3.6, whereas the measured pH of the fruit of the 'Honeycrisp' apple tree was 3.55.

*Titratable acid.*—Upon harvest the fruit of the new variety had a titratable acid concentration of 0.62 grams per 100 ml.; whereas the fruit of the 'Honeycrisp' apple tree had a titratable acid concentration of about 0.52 grams per 100 ml. On Jan. 23, 2012 the new variety had a calculated titratable acid concentration of 0.50 grams per 100 ml., as compared to the fruit of the 'Honeycrisp' apple tree which had a calculated titratable acid concentration of about 0.45 grams per 100 ml.

*Keeping quality.*—Considered excellent for the species. The present variety has been kept up to four months in common storage with no deleterious effects noted. The flesh of the present variety browns very little after being exposed to the atmosphere. The present variety will develop a bitter pit, similar to the fruit produced by the 'Honeycrisp' apple tree (U.S. Plant Pat. No. 7,197), after the varieties fruit has been stored for four months or longer under typical storage conditions.

*Pollination.*—The present variety may be pollinated by any diploid apple tree that blooms in approximately the same season.

*Fruit use.*—Considered a fresh dessert apple.

*Resistance to disease and insects.*—The present variety is considered to be susceptible to all insects and diseases found in the region of Central Washington state.

Although the new variety of apple tree possesses the characteristics when grown under the ecological conditions prevailing in Grant County, Wash., it is to be understood that variations of the usual magnitude and characteristics incident to changes in growing conditions, fertilization, pruning and pest control is to be expected.

Having thus described and illustrated my new variety of apple tree, what I claim is new, and desire to secure by plant Letters Patent is:

1. A new and distinct variety of apple tree as substantially illustrated and described, and which is characterized principally as to novelty by producing an attractively colored apple which is mature for harvesting and shipment on approximately October 12 under the ecological conditions prevailing in Grant County, Wash.

* * * * *